United States Patent
Deguchi et al.

(10) Patent No.: US 10,324,029 B2
(45) Date of Patent: Jun. 18, 2019

(54) CONCENTRATION MEASUREMENT DEVICE

(71) Applicants: TOKUSHIMA UNIVERSITY, Tokushima (JP); FUJIKIN INCORPORATED, Osaka (JP)

(72) Inventors: Yoshihiro Deguchi, Tokushima (JP); Masaaki Nagase, Osaka (JP); Michio Yamaji, Osaka (JP); Nobukazu Ikeda, Osaka (JP); Kouji Nishino, Osaka (JP); Masayoshi Kawashima, Osaka (JP); Kazuteru Tanaka, Osaka (JP)

(73) Assignees: TOKUSHIMA UNIVERSITY, Tokushima (JP); FUJIKIN INCORPORATED, Osaka (JP)

( * ) Notice: Subject to any disclaimer, the term of this patent is extended or adjusted under 35 U.S.C. 154(b) by 0 days.

(21) Appl. No.: 15/748,261

(22) PCT Filed: Aug. 9, 2016

(86) PCT No.: PCT/JP2016/003668
§ 371 (c)(1),
(2) Date: Jan. 29, 2018

(87) PCT Pub. No.: WO2017/029791
PCT Pub. Date: Feb. 23, 2017

(65) Prior Publication Data
US 2018/0217053 A1    Aug. 2, 2018

(30) Foreign Application Priority Data
Aug. 18, 2015    (JP) .................................. 2015-161234

(51) Int. Cl.
*G01N 21/31*    (2006.01)
*G01N 21/33*    (2006.01)
(Continued)

(52) U.S. Cl.
CPC ........ *G01N 21/3103* (2013.01); *G01J 3/0218* (2013.01); *G01J 3/10* (2013.01);
(Continued)

(58) Field of Classification Search
CPC ... G01J 3/42; G01N 2021/3133; G01N 21/03; G01N 21/3103; G01N 21/33; G01N 21/59
(Continued)

(56) References Cited

U.S. PATENT DOCUMENTS 3,923,397 A * 12/1975 Shuck .................... G01N 21/59
356/39
2002/0084416 A1    7/2002 Kiuchi
(Continued)

FOREIGN PATENT DOCUMENTS

JP    54-028683 A    3/1979
JP    06-137948 A    5/1994
(Continued)

OTHER PUBLICATIONS

International Search Report issued in PCT/JP2016/003668; dated Nov. 1, 2016.

*Primary Examiner* — Tri T Ton
(74) *Attorney, Agent, or Firm* — Studebaker & Brackett PC

(57) ABSTRACT

A concentration measurement device including at least one light source; a measurement cell for containing a fluid to be measured; a splitter for dividing light from the light source into incident light being incident into the measurement cell and non-incident light not being incident into the measurement cell; a transmitted-light detector for detecting transmitted light that is the incident light having passed through the measurement cell; a non-incident light detector for detecting the non-incident light; and an arithmetic part for (Continued)

correcting a detection signal of the transmitted-light detector using a detection signal of the non-incident light detector.

11 Claims, 6 Drawing Sheets

(51) Int. Cl.
| | |
|---|---|
| *G01J 3/42* | (2006.01) |
| *G01N 21/59* | (2006.01) |
| *G01N 21/27* | (2006.01) |
| *G01J 3/10* | (2006.01) |
| *G01J 3/28* | (2006.01) |
| *G01J 3/433* | (2006.01) |
| *G01J 3/02* | (2006.01) |
| G01N 21/3504 | (2014.01) |
| G01J 1/42 | (2006.01) |

(52) U.S. Cl.
CPC . *G01J 3/28* (2013.01); *G01J 3/42* (2013.01); *G01J 3/433* (2013.01); *G01N 21/274* (2013.01); *G01N 21/33* (2013.01); *G01N 21/59* (2013.01); *G01J 2001/4242* (2013.01); *G01J 2003/2866* (2013.01); *G01N 21/3504* (2013.01); *G01N 2021/3133* (2013.01); *G01N 2201/0625* (2013.01); *G01N 2201/0627* (2013.01)

(58) Field of Classification Search
USPC .................................. 356/432–448, 335–343
See application file for complete search history.

(56) References Cited

U.S. PATENT DOCUMENTS

| | | | |
|---|---|---|---|
| 2003/0052272 | A1 | 3/2003 | Kiuchi et al. |
| 2006/0263253 | A1* | 11/2006 | Steuerwald ............ G01N 21/05 |
| | | | 422/82.05 |
| 2012/0019815 | A1 | 1/2012 | Horikoshi et al. |
| 2016/0041095 | A1* | 2/2016 | Rothberg ........... G01N 21/6408 |
| | | | 506/4 |
| 2017/0016813 | A1* | 1/2017 | Wagner .............. G01N 21/3577 |

FOREIGN PATENT DOCUMENTS

| | | |
|---|---|---|
| JP | 07-077492 A | 3/1995 |
| JP | 08-101123 A | 4/1996 |
| JP | 08-320285 A | 12/1996 |
| JP | 09-304274 A | 11/1997 |
| JP | 2000-206045 A | 7/2000 |
| JP | 2002-139428 A | 5/2002 |
| JP | 2002-340676 A | 11/2002 |
| JP | 2012-026746 A | 2/2012 |
| JP | 2015-049168 A | 3/2015 |
| WO | 01/053803 A1 | 7/2001 |

* cited by examiner

Time

Time

CONCENTRATION MEASUREMENT DEVICE

TECHNICAL FIELD

The present invention relates to a concentration measurement device for measuring gas concentration based on the principal of absorption spectrophotometry.

BACKGROUND ART

Conventionally, a well-known concentration measurement device is integrated into a gas supply line for supplying a raw material gas such as an organic metal (MO) gas and the like to a semiconductor manufacturing equipment, to measure the concentration of the gas in the gas supply line.

In this type of concentration measurement device, concentration is obtained from absorbance that is measured by a photodetector detecting light absorbed by a gas while the gas passing through inside a measurement cell provided in a gas supply line, into which a light having a predetermined wavelength is incident from a light source.

However, errors in the measurement concentration occur under the influence of the ambient environment such as temperature, and the fluctuation in light emission intensity of the light source or light receiving intensity of a photodetector (light receiving element) or the like. Calibration is necessary to maintain the measurement accuracy, but the gas supply line of the semiconductor manufacturing equipment needs to be calibrated while avoiding contact with outside to prevent contamination.

For that reason, an in-line system concentration measurement device has been suggested to include a measurement cell providing a fluid to be measured, a calibration cell having similar characteristics to the measurement cell providing a fluid for calibration, a light source projecting light switchable to one of the two cells selectively, a light receiver receiving light having passed through inside the cell (for example, patent document 1, etc.).

PRIOR ART DOCUMENT

Patent Document

Patent document 1: Japanese Unexamined Patent Publication No. 2000-206045

SUMMARY OF THE INVENTION

Problem to be Solved by the Invention

However, there is a problem in the above-mentioned conventional concentration measurement device that real-time measurement cannot be performed because both the measurement cell and the calibration cell need to use the same light source and the same light receiver, and because the structure is complicated due to the necessity of switching between the two cells for measurement.

Therefore, a main object of the present invention is to provide a concentration measurement device capable of accurately correcting errors in the real-time measured concentration without any complicated structure.

Means for Solving the Problem

In order to achieve the above-mentioned purpose, a first aspect of the concentration measurement device according to the present invention comprises at least one light source; a measurement cell for containing a fluid to be measured; a splitter for dividing light from the light source into incident light being incident into the measurement cell and non-incident light not being incident into the measurement cell; a transmitted-light detector for detecting transmitted light, that is the incident light having passed through the measurement cell; a non-incident light detector for detecting the non-incident light; and an arithmetic part for correcting a detection signal of the transmitted-light detector using a detection signal of the non-incident light detector.

Additionally, in accordance with the above-mentioned first aspect of the present invention, in a second aspect of the concentration measurement device, the light source includes a plurality of light sources emitting lights having different wavelengths respectively; and at least one multiplexer is further provided for multiplexing the plurality of lights having different wavelengths emitted by the plurality of light-emitting elements before the lights are divided by the splitter.

Moreover, a third aspect of the concentration measurement device according to the present invention comprises a plurality of light sources for emitting lights of different wavelengths respectively; a measurement cell for containing a fluid to be measured; at least one multiplexer for multiplexing the plurality of lights having different wavelengths emitted by the plurality of light sources; a transmitted-light detector for detecting transmitted light that has been multiplexed and passed through the measurement cell; a non-incident light detection port provided on the multiplexer for taking out a part of the light from the light source as non-incident light not being incident into the measurement cell; an arithmetic part for correcting a detection signal of the transmitted-light detector using a detection signal at the non-incident light detection port.

In accordance with the above-mentioned third aspect of the present invention, in a fourth aspect of the concentration measurement device, a slit is further provided at the non-incident light detection port for allowing the non-incident light to pass through.

In accordance with the above-mentioned first or third aspect of the present invention, in a fifth aspect of the concentration measurement device, the arithmetic part corrects the detection signal of the transmitted-light detector by computation based on the equation below.

$$I_{cor} = I_{cell} \times (I_{ref,0}/I_{ref})$$

Where, $I_{cor}$ is corrected light intensity of the transmitted-light detector, $I_{ref,0}$ is initial intensity of the non-incident light detected by the non-incident light detector, $I_{cell}$ is light intensity detected by the transmitted-light detector at the time of measurement, $I_{ref}$ is light intensity detected by the non-incident light detector at the time of measurement.

In accordance with the above-mentioned second or third aspect of the present invention, a sixth aspect of the concentration measurement device comprises an oscillation circuit device for feeding driving currents of different frequencies to the plurality of light sources respectively.

In accordance with the above-mentioned sixth aspect of the present invention, in a seventh aspect of the concentration measurement device, computation by the arithmetic part includes a process of frequency analysis of the detection signal of the transmitted-light detector by using a fast Fourier transform.

In accordance with the above-mentioned sixth aspect of the present invention, in an eighth aspect of the concentration measurement device, computation by the arithmetic part includes a process of frequency analysis of the detection signal of the non-incident light by using the fast Fourier transform.

In accordance with the above-mentioned first aspect of the present invention, in a ninth aspect of the concentration measurement device, the light sources include a light source emitting ultraviolet light.

In accordance with the above-mentioned first aspect of the present invention, in a tenth aspect of the concentration measurement device, the arithmetic part does not correct the detection signal of the transmitted-light detector, when there is no change in the detection signal of the non-incident light detector.

Effect of the Invention

According to the present invention, a cell for calibration is not needed. By correcting the detection signal of the transmitted-light detector using the detection signal of the non-incident light, measurement concentration can be corrected in real time, and measurement accuracy can be maintained.

DESCRIPTION OF THE EMBODIMENTS

A first embodiment of the concentration measurement device according to the present invention will be described with reference to FIGS. 1 to 4.

Figure 1:
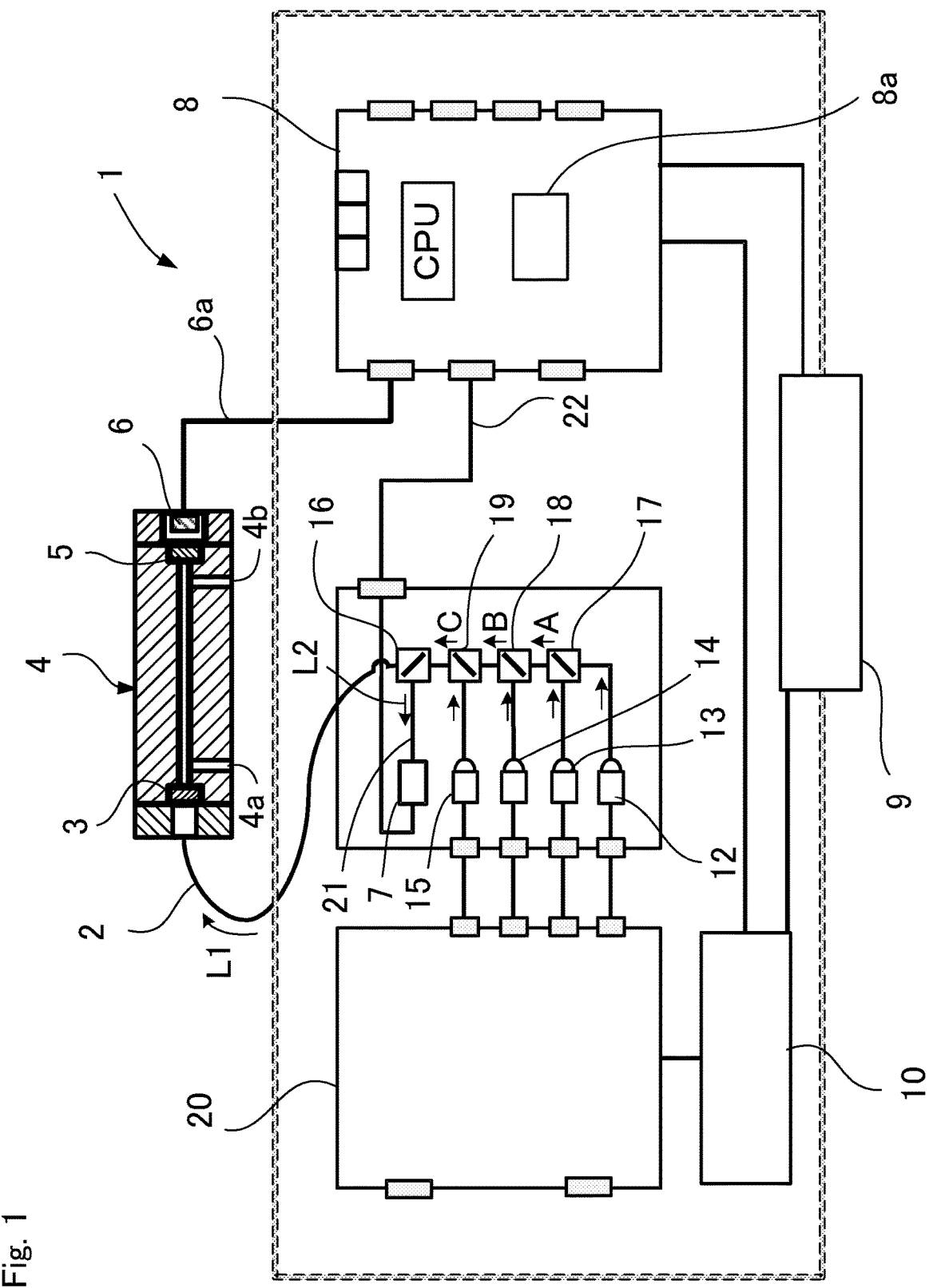
FIG. 1 is a schematic block diagram showing the first embodiment of the concentration measurement device according to the present invention.

As shown in FIG. 1, a concentration measurement device 1 comprises: a measurement cell 4 for feeding a fluid to be measured; light sources 12 to 15; a splitter 16 for dividing lights from the light sources 12 to 15 into an incident light L1 being incident into the measurement cell 4 and an non-incident light L2 not being incident into the measurement cell 4; a transmitted-light detector 6 for detecting transmitted light having passed through the measurement cell 4; a non-incident light detector 7 for detecting the non-incident light L2; and an arithmetic part 8a for correcting a detection signal of the transmitted-light detector 6 by using changes in a detection signal of the non-incident light detector 7.

The measurement cell 4 is provided with an inlet 4a and an outlet 4b for the fluid to be measured, and with a light incidence window 3 and a light emission window 5 disposed opposing to each other at both ends. As materials used for the light incidence window 3 and the light emission window 5, sapphire glass having resistance also to ultraviolet light or the like, and having mechanical and chemical stability is preferred, but other stable materials such as quartz glass can also be used.

The light sources 12 to 15 are LEDs generating lights having different wavelengths respectively, and are fed by driving currents of different frequencies respectively. As described later, since the transmitted-light detector 6 and the non-incident light detector 7 cannot detect differences in wavelengths, driving currents of different frequencies are fed to the respective light sources 12 to 15, so that the light sources 12 to 15 having different wavelengths can be distinguished from the detection signals detected by the transmitted-light detector 6 and the non-incident light detector 7.

Figure 2:
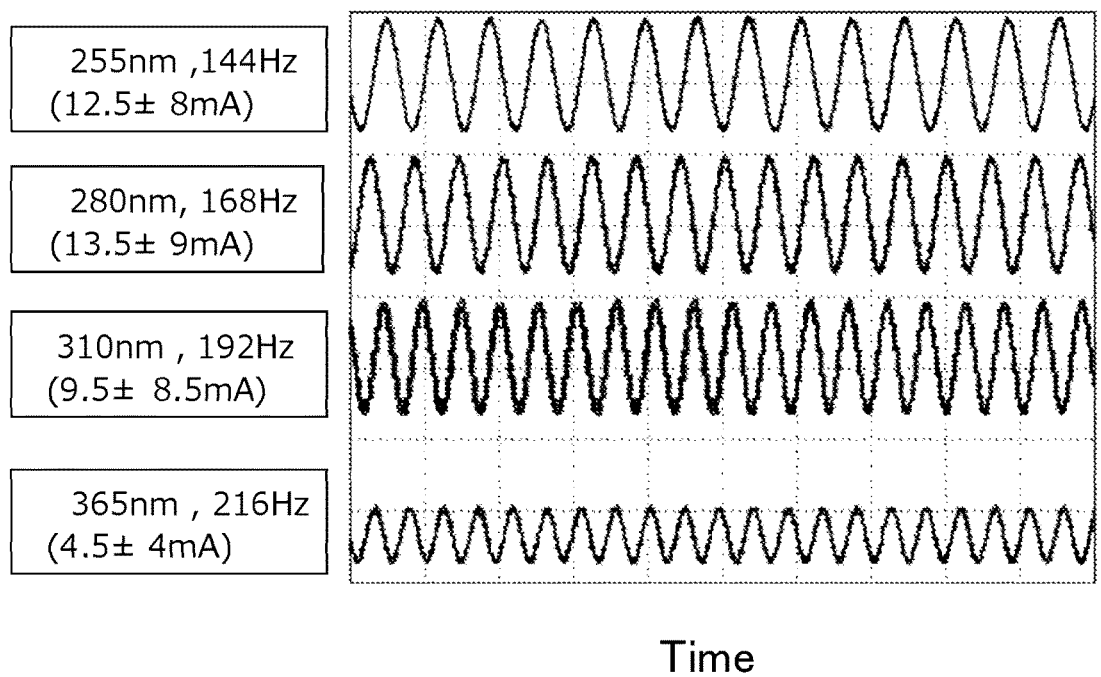
FIG. 2 is a waveform chart showing waveforms of lights generated when driving currents of different frequencies are fed to a plurality of light sources having different wavelengths respectively.

In the illustrated example, the wavelength of the light from the light source 12 is 365 nm, the wavelength of the light from the light source 13 is 310 nm, the wavelength of the light from the light source 14 is 280 nm, the wavelength of the light from the light source 15 is 255 nm, the frequency of the driving current for the light source 12 is 216 Hz, the frequency of the driving current for the light source 13 is 192 Hz, the frequency of the driving current for the light source 14 is 168 Hz, and the frequency of the driving current for the light source 15 is 144 Hz, FIG. 2 shows waveforms of the light sources 12 to 15 respectively.

Figure 3:
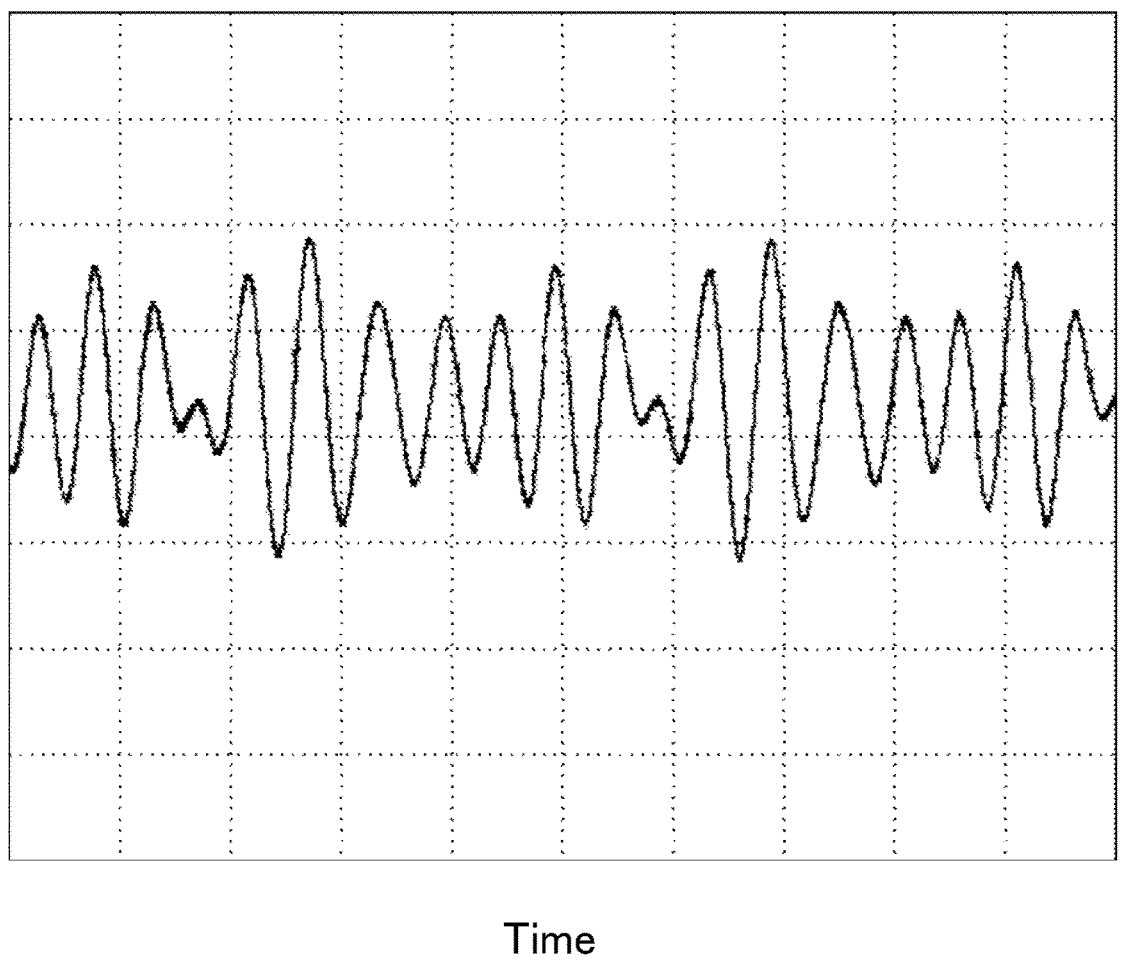
FIG. 3 is a waveform chart showing a waveform of a light obtained by multiplexing the plurality of waveforms having different wavelengths indicated in FIG. 2 by a multiplexer.

The lights having a plurality of wavelengths emitted by the light sources 12 to are multiplexed by WDM (Wavelength Division Multiplexing) multiplexers 17 to 19 respectively. The multiplexer 17 multiplexes the light from the light source 12 and the light from the light source 13 to output a multiplexed light A. The multiplexer 18 multiplexes the light from the light source 14 and the multiplexed light A to output a multiplexed light B. The multiplexer 19 multiplexes the multiplexed light B and the light from the light source 15 to make a multiplexed light C. Therefore, the multiplexed light C includes four different wavelengths. FIG. 3 shows a waveform of the multiplexed light C detected by a photodiode.

The multiplexed light C is guided through an optical fiber 2, made as parallel rays via a collimator (not illustrated) to penetrate the light incidence window 3, and is incident into the measurement cell 4. The numeral 20 represents an oscillation circuit device for feeding driving currents of different frequencies to the light sources 12 to 15 respectively.

The light having passed through the measurement cell 4 penetrates the emission window 5 to be received by the transmitted-light detector 6. The transmitted-light detector 6 is provided with a light sensor such as a photodiode, or a phototransistor, or the like as a light receiving element. When irradiated by the transmitted light having passed through the measurement cell 4, the transmitted-light detector 6 outputs a detected voltage signal proportional to the transmitted light to an arithmetic control unit 8 through a wiring 6a.

In the illustrated example, the transmitted-light detector 6 is installed in the measurement cell 4. However, in order to avoid the influence of heat transmitted from the gas within the measurement cell to the light receiving element of the transmitted-light detector 6, the light receiving element can also be disposed in a position apart from the measurement cell 4 to receive the transmitted light from the measurement cell 4 via a collimator and an optical fiber (not illustrated) connected to the outside of the light emission window 5 of the measurement cell 4.

The splitter 16 divides a part of the multiplexed light C (for example, a predetermined proportion of 25 to 35%) as the non-incident light L2 not being incident into the measurement cell 4. The divided non-incident light L2 is transmitted by an optical fiber 21 to be received by the non-incident light detector 7. The detection signal of the non-incident light detector 7 is output as an electrical signal to the arithmetic control unit 8 through an electric wiring 22. The non-incident light detector 7 may be provided with a light receiving element similar to the transmitted-light detector 6.

In the arithmetic part 8a of the arithmetic control unit 8, the concentration of the fluid to be measured is calculated from the detection signal of the light detected by the transmitted-light detector 6 based on the absorptiometry. The arithmetic control unit 8 indicates the calculated concentration on a display 9 such as a liquid crystal panel.

Figure 4:
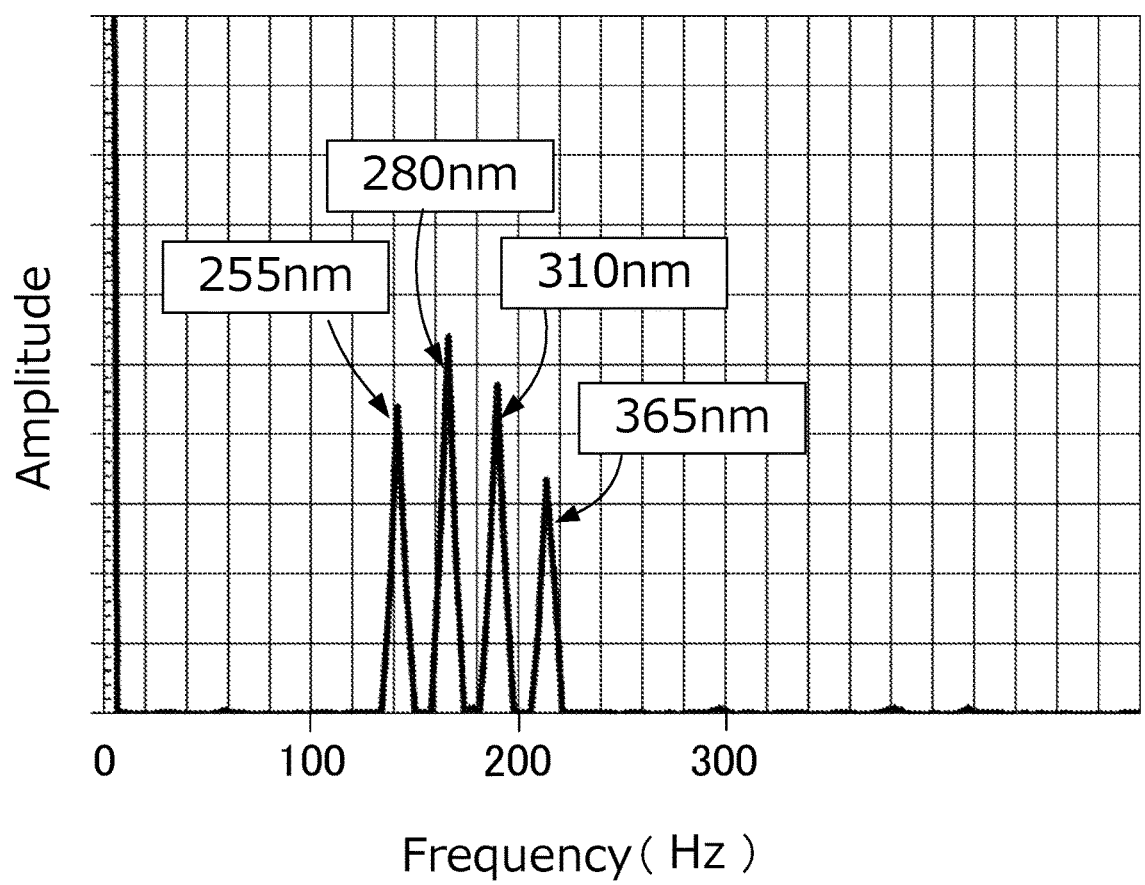
FIG. 4 is a spectrography showing an amplitude spectrum after frequency analysis of the waveform data indicated in FIG. 3 by the fast Fourier transform.

The transmitted-light detector 6 detects the light obtained by multiplexing a plurality of frequencies, and the detection signal of the multiplexed light is A/D converted as a digital signal, transmitted to the arithmetic part 8a, subjected to a frequency analysis with the arithmetic part 8a by a fast Fourier transform, and converted to amplitude spectra of the respective frequency components. FIG. 4 is a spectrography showing the amplitude spectra after a frequency analysis by the fast Fourier transform. In FIG. 4, the frequency on the horizontal axis represents the frequency of the driving current, while the amplitude on the vertical axis represents the light intensity. FIG. 4 represents a state when no fluid to be measured having light absorption characteristics is fed, or a state when no light absorption is found (hereinafter referred to as "no-absorption state"), such as a state when a no-light-absorption nitrogen gas is fed. When an organic metal material is fed into the measurement cell 4 as the fluid to be measured, the amplitude of the frequency of the wavelength where absorption is found decease in the spectrography shown in FIG. 4.

From the change in amplitude of the amplitude spectrum of the wavelength where absorption is found, based on the Lambert-Bees's, absorbance $A_\lambda$ can be calculated by equation (1) below for determining absorbance $A_\lambda$.

$$A_\lambda = \log_{10}(I_0/I) = \alpha LC \quad (1)$$

Where $I_0$ is intensity of the incident light that is incident into the measurement cell, I is intensity of the transmitted light having passed through the measurement cell, a is molar absorptivity (m²/mol), L is optical path length (m) of the measurement cell, and C is concentration (mol/m³). The molar absorptivity α is a coefficient determined by the substance.

That is, the absorbance $A_\lambda$ can be calculated by considering ($I_0/I$) in equation (1) above the change ($P_0/P$) between the amplitude peak value ($P_0$) of the amplitude spectrum at the no-absorption state and the amplitude peak value (P) of the amplitude spectrum at the time of concentration measurement shown in FIG. 4. Once the absorbance $A_\lambda$ is determined, the concentration C of the fluid to be measured can be calculated from equation (1) above.

The amplitude peak value ($P_0$) of the amplitude spectrum at the no-absorption state can be stored in advance in a memory or the like in the arithmetic control unit 8 for each frequency of the driving currents.

The detection signal by the non-incident light detector 7 for the non-incident light L2 obtained by dividing the multiplexed light is also A/D converted as a digital signal, transmitted to the arithmetic part 8a, subjected to a frequency analysis by the fast Fourier transform in the arithmetic part 8a, and converted to amplitude spectra of the respective frequency components. The initial amplitude peak value ($S_0$) of the amplitude spectrum is recorded in a memory or the like in the arithmetic control unit 8 for each frequency, and is used for the concentration correction described later.

The non-incident light L2 detected by the non-incident light detector 7 has not passed through the measurement cell 4, so it is not subjected to the absorption by the fluid to be measured. It is considered that the rate of change ($I_{ref}/I_{ref,0}$) from the initial intensity ($I_{ref,0}$) of the light detected by the non-incident light detector 7 to the light intensity ($I_{ref}$) detected by the non-incident light detector 7 at the time of measurement after a lapse of time are results from changes in the ambient environment typically temperatures, aged deterioration of optical elements, changes in emission intensity before the drive for the light source becomes stabilized, changes in light receiving intensity of the light incident photodetector, and other factors. Hence, by multiplying the reciprocal ($I_{ref,0}/I_{ref}$) of the rate of change ($I_{ref}/I_{ref,0}$) with the light intensity ($I_{cell}$) at the time of measurement by the transmitted-light detector 6, the detection signal of the transmitted-light detector 6 can be corrected.

Therefore, the arithmetic part 8a can correct the detection signal of the transmitted-light detector 6 based on equation (2) below.

$$I_{cor} = I_{cell} \times (I_{ref,0}/I_{ref}) \quad (2)$$

In equation (2) above, $I_{cor}$ is corrected light intensity of the transmitted-light detector 6, $I_{ref,0}$ is initial intensity of the non-incident light L2 detected by the non-incident light detector 7, $I_{cell}$ is light intensity at the time of measurement detected by the transmitted-light detector 6, and $I_{ref}$ is light intensity at the time of measurement detected by the non-incident light detector 7. It should be noted that the initial intensity $I_{ref}$ can be measured simultaneously with the measurement of the amplitude peak value ($P_0$) described above.

It should be noted that because of the temperature dependency of the components and temperature change of the fluid to be measured, a temperature detector may be installed in a suitable position, so that the output value (concentration measurement value) can be corrected in accordance with the measured temperature.

In this embodiment as described above, the detection signal of the non-incident light detector 7 is converted into an amplitude spectrum by the fast Fourier transform. The initial value ($S_0$) of the peak value of the amplitude spectrum of the non-incident light detector 7 is stored in a memory or the like as described above. When the light intensity detected by the non-incident light detector 7 decreases due to aged deterioration or the like of the optical elements caused by a lapse of time, the peak value (S) of the amplitude spectrum decreases. This rate of change ($S/S_0$) can be considered as the rate of change ($I_{ref}/I_{ref,0}$) in light intensity shown in the above-mentioned equation (2). Therefore, the corrected light intensity ($I_{cor}$) of the transmitted-light detector 6 can be obtained by multiplying the reciprocal ($S_0/S$) of the rate of change ($S_0/S$) with the light intensity ($I_{cell}$) detected by the transmitted-light detector 6.

By replacing the light intensity ($I_{cell}$) detected by the transmitted-light detector 6 with the amplitude peak value (P) of the amplitude spectrum at the time of concentration measurement described above, and substituting it in equation (1) above, the corrected concentration can be calculated by equation 3 below.

$$\text{Log}_{10}(P_0/(P \times (S_0/S))) = \alpha LC \quad (3)$$

In this embodiment, correction can be made for four wavelengths respectively. Since absorption spectrum varies depending on the type of gas, concentration measurement with higher accuracy becomes possible by combining wavelengths having absorptivity and wavelengths having no absorptivity. In accordance with the type of gas to be measured, it is possible to make corrections for not all wavelengths respectively, but only required wavelengths out of a plurality of wavelengths, for example, for only 2 types of wavelengths out of 4 wavelengths. The corrected concentration can be indicated on the display 9.

When there is no change in the detection signal of the non-incident light detector 7, the arithmetic part 8a can leave the detection signal of the transmitted-light detector 6 uncorrected. Herein, cases when there is no change in the detection signal include the case when there is no variation in the detection signal, and the case when the variation in the detection signal is within a certain range.

It should be noted that because of the temperature dependency of the component apparatus and temperature change of the fluid to be measured, a temperature detector may be installed in a suitable position, so that the output value (concentration measurement value) can be corrected in accordance with the measured temperature.

According to the concentration measurement device having the above-mentioned components, it is unnecessary to provide a calibration cell separately. The real-time correction of measurement concentration and the long-time maintenance of measurement accuracy can be made by correcting the detection signal of the transmitted-light detector using the change in the detection signal of the non-incident light detector 7.

In addition, since the correction method is defined by software program processing, and the correction program can be modified by rewriting the program, the extensiveness of correction is high. Moreover, by using the same type of circuits in the transmitted-light detector 6 and the non-incident light detector 7, and measuring at the same timing, successive intensity correction can be performed, and correction accuracy can be increased.

Figure 5:
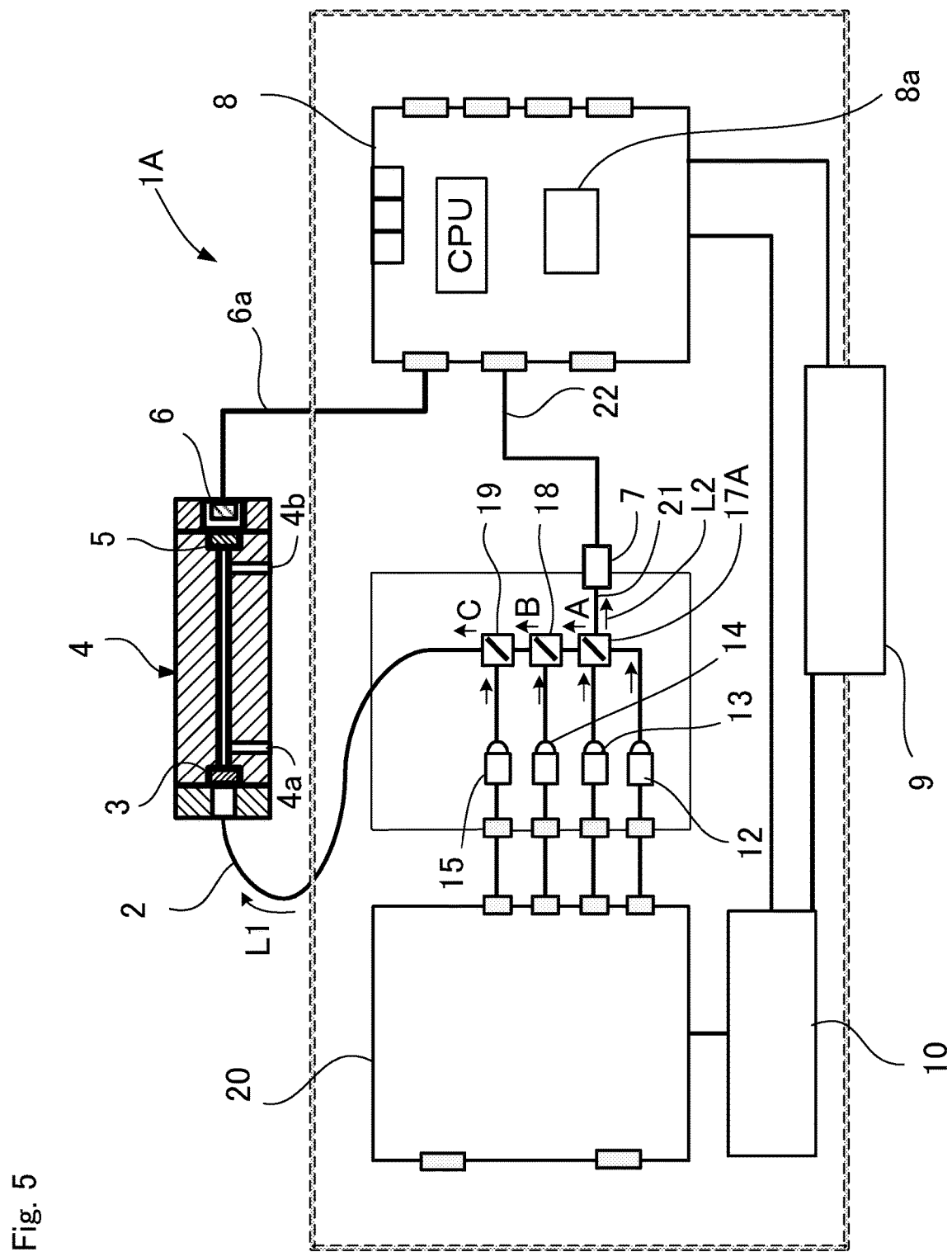
FIG. 5 is a schematic block diagram showings a second embodiment of the concentration measurement device according to the present invention.
Figure 6:
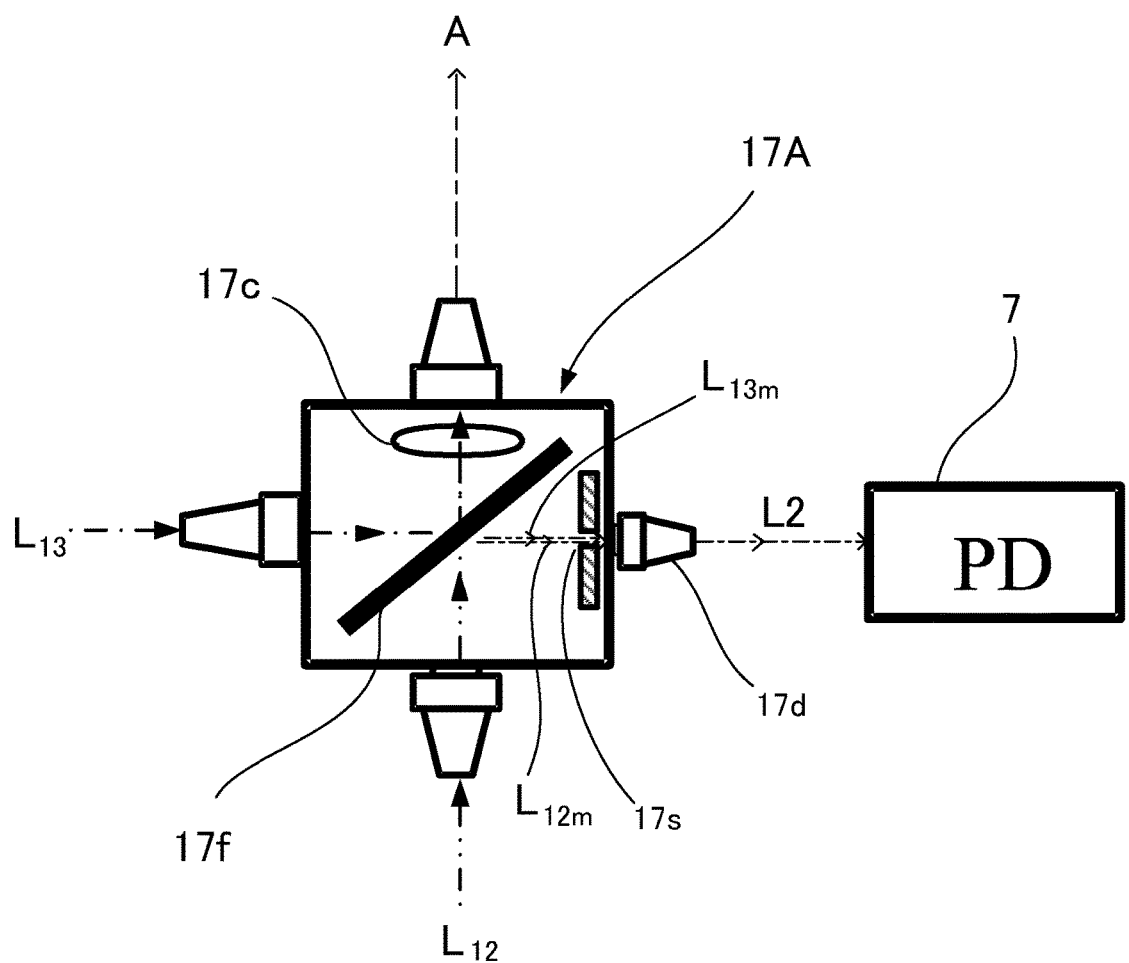
FIG. 6 is an enlarged view showing an internal structure of one of the multiplexers that are components of the second embodiment.

Next, a second embodiment of the present invention of will be described with reference to FIGS. 5 and 6. It should be noted that the same component elements in the above-mentioned first embodiment will be denoted by the same numerals and detailed explanation will be omitted. FIG. 5 shows a concentration measurement device of the second embodiment, and FIG. 6 is an enlarged view showing the internal structure of a multiplexer 17A shown in FIG. 5.

With reference to FIG. 5, a multiplexer 17A provided in the second embodiment is configured to multiplex lights $L_{12}$, $L_{13}$ coming from the light sources 12, 13 by an optical filter 17f. The light $L_{13}$ on the adding side is bent to 90 degrees by being irradiated from 45 degrees inclined to the optical filter 17f, and is multiplexed with the light $L_{12}$ having a different wavelength. A numeral 17c represents a condenser lens such as a collimator lens.

At this point, the optical filter 17f does not reflect all of the light L13. A part of the light $L13_m$ penetrates the optical filter 17f and passes straight forward. Similarly, not 100% of the light $L_{12}$, that is the original light of the multiplexed light A, penetrates the optical filter 17f and passes straight forward, a part of the light $L_{12m}$ is flashed back by the optical filter 17f. The light $L13_m$ passing straight through the optical filter 17f and the light $L_{12m}$ flashed back by the optical filter 17f are taken out from a non-incident light detection port 17d and detected by the non-incident light detector 7 as a reference light (non-incident light not being incident into the measurement cell 4).

In addition, when the non-incident light L2 is taken out from the multiplexer 17A, a slit 17s is provided at the non-incident light detection port 17d on the light incident side to eliminate scattered light within the multiplexer 17A. It should be noted that, non-incident light detection port may be installed in any one or more multiplexers when multiple multiplexers are provided.

According to the above-mentioned configuration of the multiplexer 17A, a concentration measurement device 1A in the second embodiment does not require the splitter 16 as provided on the concentration measurement device 1 in the first embodiment. Other components in the second embodiment are similar to the above-mentioned first embodiment, thus detailed explanation will be omitted.

Interpretation of the present invention should not be limited to the above-mentioned embodiments. Various modifications can be made within the range of not deviating from the purpose of the present invention. For example, lights having wavelength ranges other than ultraviolet range may also be used for measurement.

In addition, light-emitting devices other than LED, for example, LD (laser diode) may also be used as the light sources. The light receiving elements used for the transmitted-light detector 6 and the non-incident light detector 7 are not limited to photodiodes. Others such as phototransistors can also be used.

Besides, in the above-mentioned first embodiment, the multiplexed light of a plurality of different wavelengths is used as the light source, but a light source having a single wavelength can also be used. In this case, the multiplexers and the fast Fourier transform can be omitted.

Moreover, in the above-mentioned embodiments, the configuration of feeding the fluid to be measured into the measurement cell was described as an example, but a configuration of detecting concentration by sealing the measurement cell containing the fluid to be measured can be also employed.

Furthermore, in the above-mentioned embodiments, the correction of the detection signal of the transmitted-light detector 6 using the change in light intensity at the time of measurement and the initial intensity of the non-incident light L2 detected by the non-incident light detector 7 was described as an example, but correction methods are not limited to this. Other methods such as, the method of adding or subtracting difference of change in light intensity, the method of normalizing light intensity, or the method of using inclination relative to the time of change in light intensity, can be also applied.

DESCRIPTION OF REFERENCE NUMERALS 1, 1A Concentration measurement device
4 Measurement cell
6 Transmitted-light detector
7 Non-incident light detector
8a Arithmetic part
12,13,14,15 Light sources
16 Splitter
17, 17A, 18, 19 Multiplexers
17d Non-incident light detection port
17s Slit
G Fluid to be measured
L1 Incident light
L2 Non-incident light

The invention claimed is:

1. A concentration measurement device comprising:
   at least one light source;
   a measurement cell for containing a fluid to be measured;
   a splitter for dividing light from the light source into incident light being incident into the measurement cell and non-incident light not being incident into the measurement cell;
   a transmitted-light detector for detecting transmitted light that is the incident light having passed through the measurement cell;
   a non-incident light detector for detecting the non-incident light; and
   a processor for correcting a detection signal of the transmitted-light detector using a detection signal of the non-incident light detector,
   wherein the processor corrects the detection signal of the transmitted-light detector by the computation based on an equation $$Icor=Icell \times (Iref,0/Iref),$$

wherein, Icor is corrected light intensity of the transmitted-light detector, Iref,0 is initial intensity of the non-incident light detected by the non-incident light detector, Icell is light intensity at the time of measurement of the transmitted light detected by the transmitted-light detector, Iref is light intensity at the time of measurement of the non-incident light detected by the non-incident light detector.

2. The concentration measurement device according to claim 1, wherein the light source includes a plurality of light sources emitting lights of different wavelengths respectively, further comprising at least one multiplexer for multiplexing the lights of a plurality of different wavelengths emitted by the plurality of light sources before the lights are divided by the splitter.

3. A concentration measurement device comprising:
   a plurality of light sources emitting lights of different wavelengths respectively;
   a measurement cell for containing a fluid to be measured;
   at least one multiplexer for multiplexing the lights of a plurality of different wavelengths emitted by the plurality of light sources;
   a transmitted-light detector for detecting transmitted light that has been multiplexed and passed through the measurement cell;
   a non-incident light detection port provided on the multiplexer for taking out a part of the light from the light source as non-incident light not being incident into the measurement cell; and
   a processor for correcting a detection signal of the transmitted-light detector using a detection signal at the non-incident light detection port wherein the processor corrects the detection signal of the transmitted-light detector by the computation based on an equation $$Icor=Icell \times (Iref,0/Iref),$$

wherein, Icor is corrected light intensity of the transmitted-light detector, Iref,0 is initial intensity of the non-incident light detected by the non-incident light detector, Icell is light intensity at the time of measurement of the transmitted light detected by the transmitted-light detector, Tref is light intensity at the time of measurement of the non-incident light detected by the non-incident light detector.

4. The concentration measurement device according to claim 3, wherein a slit for allowing the non-incident light to pass through is further provided at the non-incident light detection port.

5. The concentration measurement device according to claim 2, further comprising an oscillation circuit device for feeding driving currents of different frequencies to the plurality of light sources respectively.

6. The concentration measurement device according to claim 5, wherein computation by the processor includes a process of frequency analysis of the detection signal of the transmitted-light detector using a fast Fourier transform.

7. The concentration measurement device according to claim 5, wherein computation by the processor includes a process of frequency analysis of the detection signal of the non-incident light using a fast Fourier transform.

8. The concentration measurement device according to claim 1, wherein the light source include a light element emitting ultraviolet light.

9. The concentration measurement device according to claim 1, wherein the processor does not correct the detection signal of the transmitted-light detector, when there is no change in the detection signal of the non-incident light detector.

10. The concentration measurement device according to claim 3, further comprising an oscillation circuit device for feeding driving currents of different frequencies to the plurality of light sources respectively.

11. The concentration measurement device according to claim 1, wherein the processor determines a concentration of the fluid based on the corrected light intensity.

* * * * *